(12) United States Patent
Miethke et al.

(10) Patent No.: US 9,295,821 B2
(45) Date of Patent: Mar. 29, 2016

(54) CEREBROSPINAL FLUID DRAINAGE

(71) Applicants: Christoph Miethke, Potsdam (DE); Ullrich Meier, Berlin (DE)

(72) Inventors: Christoph Miethke, Potsdam (DE); Ullrich Meier, Berlin (DE)

( * ) Notice: Subject to any disclaimer, the term of this patent is extended or adjusted under 35 U.S.C. 154(b) by 49 days.

(21) Appl. No.: 14/106,145

(22) Filed: Dec. 13, 2013

(65) Prior Publication Data
US 2014/0188032 A1 Jul. 3, 2014

Related U.S. Application Data

(63) Continuation of application No. 12/981,224, filed on Dec. 29, 2010, now abandoned.

(51) Int. Cl.
*A61M 27/00* (2006.01)

(52) U.S. Cl.
CPC ..... *A61M 27/006* (2013.01); *A61M 2202/0464* (2013.01); *A61M 2210/0693* (2013.01)

(58) Field of Classification Search
CPC ................... A61M 27/006; A61M 2202/0464; A61M 2210/0693
See application file for complete search history.

(56) References Cited

U.S. PATENT DOCUMENTS

| | | |
|---|---|---|
| 111,659 A | 2/1871 | Mackay |
| 3,583,387 A | 6/1971 | Garner |
| 3,595,240 A | 7/1971 | Mishler |
| 3,601,128 A | 8/1971 | Hakim |
| 3,886,948 A | 6/1975 | Hakim |
| 3,999,551 A | 12/1976 | Spitz et al. |
| 4,000,739 A | 1/1977 | Stevens |
| 4,014,333 A | 3/1977 | McIntyre |
| 4,084,606 A | 4/1978 | Mittleman |
| 4,092,999 A | 6/1978 | Rubrich |
| 4,103,689 A | 8/1978 | Leighton |
| 4,106,510 A | 8/1978 | Hakim et al. |
| 4,127,110 A | 11/1978 | Bullara |
| 4,156,422 A | 5/1979 | Hildebrandt et al. |
| 4,156,442 A | 5/1979 | Sykes |
| 4,166,469 A | 9/1979 | Littleford |

(Continued)

FOREIGN PATENT DOCUMENTS

| | | |
|---|---|---|
| CH | 496445 | 9/1970 |
| DE | 1994587 | 9/1968 |

(Continued)

OTHER PUBLICATIONS

International Search Report PCT/EP2009/004751 and English translation thereof.

*Primary Examiner* — Philip R Wiest
*Assistant Examiner* — Benjamin Klein
(74) *Attorney, Agent, or Firm* — Nils H. Ljungman & Associates

(57) ABSTRACT

A cerebrospinal fluid drainage. The abstract of the disclosure is submitted herewith as required by 37 C.F.R. §1.72(b). As stated in 37 C.F.R. §1.72(b): A brief abstract of the technical disclosure in the specification must commence on a separate sheet, preferably following the claims, under the heading "Abstract of the Disclosure." The purpose of the abstract is to enable the Patent and Trademark Office and the public generally to determine quickly from a cursory inspection the nature and gist of the technical disclosure. The abstract shall not be used for interpreting the scope of the claims. Therefore, any statements made relating to the abstract are not intended to limit the claims in any manner and should not be interpreted as limiting the claims in any manner.

18 Claims, 5 Drawing Sheets

(56) References Cited

U.S. PATENT DOCUMENTS

| | | |
|---|---|---|
| 4,167,952 A | 9/1979 | Reinicke |
| 4,186,749 A | 2/1980 | Fryer |
| 4,190,040 A | 2/1980 | Schulte |
| 4,206,761 A | 6/1980 | Cosman |
| 4,206,762 A | 6/1980 | Cosman |
| 4,215,695 A | 8/1980 | Spitz et al. |
| 4,240,434 A | 12/1980 | Newkirk |
| 4,246,930 A | 1/1981 | Bishop et al. |
| 4,248,234 A | 2/1981 | Assenza et al. |
| 4,256,093 A | 3/1981 | Helms et al. |
| 4,261,341 A | 4/1981 | Hakim et al. |
| 4,281,666 A | 8/1981 | Cosman |
| 4,281,667 A | 8/1981 | Cosman |
| 4,300,571 A | 11/1981 | Waldbillig |
| 4,331,179 A | 5/1982 | Gray |
| 4,332,255 A | 6/1982 | Hakim et al. |
| 4,332,555 A | 6/1982 | Richardson |
| 4,340,038 A | 7/1982 | McKean |
| 4,342,218 A | 8/1982 | Fox |
| 4,354,492 A | 10/1982 | McPhee |
| 4,360,007 A | 11/1982 | Levy et al. |
| 4,364,395 A | 12/1982 | Redmond et al. |
| 4,375,816 A | 3/1983 | Labianca |
| 4,382,445 A | 5/1983 | Sommers |
| 4,387,715 A | 6/1983 | Hakim et al. |
| 4,413,985 A | 11/1983 | Wellner et al. |
| 4,416,273 A | 11/1983 | Grimes |
| 4,428,397 A | 1/1984 | Bron |
| 4,430,081 A | 2/1984 | Timmermans |
| 4,437,493 A | 3/1984 | Okuda et al. |
| 4,443,214 A | 4/1984 | Marion |
| 4,450,710 A | 5/1984 | Nettekoven |
| 4,451,128 A | 5/1984 | Fruengel |
| 4,452,423 A | 6/1984 | Beblavi et al. |
| 4,464,168 A | 8/1984 | Redmond et al. |
| 4,465,482 A | 8/1984 | Tittel |
| 4,468,224 A | 8/1984 | Enzmann et al. |
| 4,474,569 A | 10/1984 | Newkirk |
| 4,475,898 A | 10/1984 | Brodner et al. |
| 4,475,899 A | 10/1984 | Muller |
| 4,501,580 A | 2/1985 | Glassman |
| 4,515,012 A | 5/1985 | Jenkins et al. |
| 4,524,794 A | 6/1985 | Haines |
| 4,540,400 A | 9/1985 | Hooven |
| 4,541,429 A | 9/1985 | Prosl et al. |
| 4,546,642 A | 10/1985 | Swanson |
| 4,547,192 A | 10/1985 | Brodsky et al. |
| 4,551,128 A | 11/1985 | Hakim et al. |
| 4,552,553 A | 11/1985 | Schulte et al. |
| 4,553,956 A | 11/1985 | Muller |
| 4,554,918 A | 11/1985 | White |
| 4,557,721 A | 12/1985 | Hooven |
| 4,559,046 A | 12/1985 | Groshong et al. |
| 4,560,375 A | 12/1985 | Schulte et al. |
| 4,578,057 A | 3/1986 | Sussman |
| 4,583,967 A | 4/1986 | Harris |
| 4,588,085 A | 5/1986 | Sussman |
| 4,589,287 A | 5/1986 | Dickens |
| 4,595,390 A | 6/1986 | Hakim et al. |
| 4,598,579 A | 7/1986 | Cummings et al. |
| 4,601,724 A | 7/1986 | Hooven et al. |
| 4,605,395 A | 8/1986 | Rose et al. |
| 4,606,365 A | 8/1986 | Siposs |
| 4,615,691 A | 10/1986 | Hakim et al. |
| 4,621,654 A | 11/1986 | Holter |
| 4,624,286 A | 11/1986 | Frohn |
| 4,624,647 A | 11/1986 | Munnix |
| 4,627,832 A | 12/1986 | Hooven et al. |
| 4,631,051 A | 12/1986 | Harris |
| 4,634,427 A | 1/1987 | Hannula et al. |
| 4,636,194 A | 1/1987 | Schulte et al. |
| 4,648,406 A | 3/1987 | Miller |
| 4,653,508 A | 3/1987 | Cosman |
| 4,657,530 A | 4/1987 | Buchwald et al. |
| 4,660,568 A | 4/1987 | Cosman |
| 4,673,384 A | 6/1987 | Marion |
| 4,675,003 A | 6/1987 | Hooven |
| 4,676,255 A | 6/1987 | Cosman |
| 4,676,772 A | 6/1987 | Hooven |
| 4,677,985 A | 7/1987 | Bro et al. |
| 4,681,559 A | 7/1987 | Hooven |
| 4,681,560 A | 7/1987 | Schulte et al. |
| 4,705,499 A | 11/1987 | Hooven |
| 4,714,458 A | 12/1987 | Hooven |
| 4,714,459 A | 12/1987 | Hooven |
| 4,723,556 A | 2/1988 | Sussman |
| 4,729,762 A | 3/1988 | Doumenis |
| 4,733,566 A | 3/1988 | Moriuchi et al. |
| 4,735,607 A | 4/1988 | Keith, Jr. |
| 4,738,267 A | 4/1988 | Lazorthes et al. |
| 4,739,771 A | 4/1988 | Manwaring |
| 4,741,730 A | 5/1988 | Dormandy, Jr. et al. |
| 4,749,003 A | 6/1988 | Leason |
| 4,761,158 A | 8/1988 | Schulte et al. |
| 4,767,400 A | 8/1988 | Miller et al. |
| 4,769,002 A | 9/1988 | Hooven |
| 4,772,257 A | 9/1988 | Hakim et al. |
| 4,776,838 A | 10/1988 | Sainte-Rose et al. |
| 4,776,839 A | 10/1988 | Doumenis |
| 4,779,614 A | 10/1988 | Moise |
| 4,781,672 A | 11/1988 | Hooven |
| 4,781,673 A | 11/1988 | Watanabe |
| 4,781,674 A | 11/1988 | Redmond et al. |
| 4,784,638 A | 11/1988 | Ghajar et al. |
| 4,787,886 A | 11/1988 | Cosman |
| 4,787,887 A | 11/1988 | Saenz Arroyo |
| 4,795,437 A | 1/1989 | Schulte et al. |
| 4,841,984 A | 6/1989 | Armeniades et al. |
| 4,850,955 A | 7/1989 | Newkirk |
| 4,861,331 A | 8/1989 | East et al. |
| 4,867,740 A | 9/1989 | East |
| 4,867,741 A | 9/1989 | Portnoy |
| 4,875,482 A | 10/1989 | Hariri et al. |
| 4,883,456 A | 11/1989 | Holter |
| 4,885,002 A | 12/1989 | Watanabe et al. |
| 4,898,583 A | 2/1990 | Borsanyi et al. |
| 4,898,584 A | 2/1990 | Borsanyi et al. |
| 4,898,585 A | 2/1990 | Borsanyi et al. |
| 4,944,307 A | 7/1990 | Hon et al. |
| 4,950,230 A * | 8/1990 | Kendell ............... 604/28 |
| 4,950,232 A | 8/1990 | Ruzicka et al. |
| 4,973,024 A | 11/1990 | Homma |
| 4,995,864 A | 2/1991 | Bartholomew et al. |
| 5,000,731 A | 3/1991 | Wong |
| 5,042,974 A | 8/1991 | Agarwal |
| 5,054,497 A | 10/1991 | Kapp et al. |
| 5,054,518 A | 10/1991 | Rancani |
| 5,069,663 A | 12/1991 | Sussman |
| 5,074,310 A | 12/1991 | Mick |
| 5,105,820 A | 4/1992 | Moriuchi et al. |
| 5,117,835 A | 6/1992 | Mick |
| 5,120,313 A | 6/1992 | Elftman |
| 5,152,753 A | 10/1992 | Laguette et al. |
| 5,167,615 A | 12/1992 | East et al. |
| 5,176,627 A | 1/1993 | Watson |
| 5,192,265 A | 3/1993 | Drake et al. |
| 5,207,684 A | 5/1993 | Nobles |
| 5,257,630 A | 11/1993 | Broitman et al. |
| 5,265,606 A | 11/1993 | Kujawski |
| 5,279,308 A | 1/1994 | DiSabito et al. |
| 5,284,138 A | 2/1994 | Kujawski |
| 5,289,827 A | 3/1994 | Orkin et al. |
| 5,304,114 A | 4/1994 | Cosman |
| 5,323,865 A | 6/1994 | Isbell et al. |
| 5,336,166 A | 8/1994 | Sierra |
| 5,345,963 A | 9/1994 | Dietiker |
| 5,368,556 A | 11/1994 | Lecuyer |
| 5,373,852 A | 12/1994 | Harrison et al. |
| 5,387,188 A | 2/1995 | Watson |
| 5,405,316 A | 4/1995 | Magram |
| 5,437,626 A | 8/1995 | Cohen et al. |
| 5,458,606 A | 10/1995 | Cohen et al. |
| 5,464,144 A | 11/1995 | Guy et al. |
| 5,497,934 A | 3/1996 | Brady et al. |

(56) References Cited

U.S. PATENT DOCUMENTS

| | | | |
|---|---|---|---|
| 5,503,320 | A | 4/1996 | Webster et al. |
| 5,520,632 | A | 5/1996 | Leveen |
| 5,566,680 | A | 10/1996 | Urion et al. |
| 5,573,007 | A | 11/1996 | Bobo, Sr. |
| 5,634,476 | A | 6/1997 | Orkin et al. |
| 5,634,894 | A | 6/1997 | Magram |
| 5,637,083 | A | 6/1997 | Bertrand et al. |
| 5,643,194 | A | 7/1997 | Negre |
| 5,643,195 | A | 7/1997 | Drevet et al. |
| 5,649,548 | A | 7/1997 | Rapp et al. |
| 5,683,357 | A | 11/1997 | Magram |
| 5,704,352 | A | 1/1998 | Tremblay et al. |
| 5,728,061 | A | 3/1998 | Ahmed |
| 5,733,157 | A | 3/1998 | Okuzawa et al. |
| 5,746,212 | A | 5/1998 | Rall et al. |
| 5,762,599 | A | 6/1998 | Sohn |
| 5,795,307 | A | 8/1998 | Krueger |
| 5,800,376 | A | 9/1998 | Watson et al. |
| 5,807,303 | A | 9/1998 | Bays |
| 5,810,761 | A | 9/1998 | Saens-Arrollo |
| 5,833,603 | A | 11/1998 | Kovacs et al. |
| 5,843,013 | A | 12/1998 | Lecuyer et al. |
| 5,846,013 | A | 12/1998 | To |
| 5,868,674 | A | 2/1999 | Glowinski et al. |
| 5,873,840 | A | 2/1999 | Neff |
| 5,911,690 | A | 6/1999 | Rall |
| 5,928,182 | A | 7/1999 | Kraus et al. |
| 5,944,023 | A | 8/1999 | Johnson et al. |
| 5,947,991 | A | 9/1999 | Cowan |
| 5,951,497 | A | 9/1999 | Wallace et al. |
| 5,964,705 | A | 10/1999 | Truwit et al. |
| 5,971,954 | A | 10/1999 | Conway et al. |
| 5,980,480 | A | 11/1999 | Rubenstein et al. |
| 5,984,879 | A | 11/1999 | Wallace et al. |
| 6,015,386 | A | 1/2000 | Kensey et al. |
| 6,018,094 | A | 1/2000 | Fox |
| 6,022,333 | A | 2/2000 | Kensey |
| 6,026,316 | A | 2/2000 | Kucharczyk et al. |
| 6,050,696 | A | 4/2000 | Radley |
| 6,061,587 | A | 5/2000 | Kucharczyk et al. |
| 6,080,134 | A | 6/2000 | Lotti et al. |
| 6,083,179 | A | 7/2000 | Oredsson |
| 6,086,533 | A | 7/2000 | Madsen et al. |
| 6,113,553 | A | 9/2000 | Chubbuck |
| 6,165,135 | A | 12/2000 | Neff |
| 6,183,421 | B1 | 2/2001 | Bobo |
| 6,214,660 | B1 | 4/2001 | Uemoto et al. |
| 6,231,524 | B1 | 5/2001 | Wallace et al. |
| 6,277,078 | B1 | 8/2001 | Porat et al. |
| 6,383,159 | B1 | 5/2002 | Saul et al. |
| 6,383,160 | B1 | 5/2002 | Madsen |
| 6,391,019 | B1 | 5/2002 | Ito |
| 6,432,058 | B1 | 8/2002 | Sloth |
| 6,447,462 | B1 | 9/2002 | Wallace et al. |
| 6,474,360 | B1 | 11/2002 | Ito |
| 6,689,085 | B1* | 2/2004 | Rubenstein et al. ............. 604/9 |
| 2003/0216666 | A1 | 11/2003 | Ericson et al. |
| 2005/0245858 | A1 | 11/2005 | Miesel et al. |
| 2005/0245887 | A1 | 11/2005 | Olsen et al. |
| 2007/0004999 | A1 | 1/2007 | Miethke |
| 2007/0078398 | A1 | 4/2007 | Dextradeur et al. |
| 2010/0030103 | A1 | 2/2010 | Lutze et al. |
| 2010/0210992 | A1* | 8/2010 | Dextradeur et al. ............. 604/9 |

FOREIGN PATENT DOCUMENTS

| | | |
|---|---|---|
| DE | 4130601 | 4/1992 |
| DE | 3486114 | 10/1993 |
| DE | 4307387 | 9/1994 |
| DE | 4401422 | 7/1995 |
| DE | 4401422 A1 | 7/1995 |
| DE | 19535637 | 3/1997 |
| DE | 19711610 | 10/1997 |
| DE | 19645725 | 12/1997 |
| DE | 19705474 | 8/1998 |
| DE | 19713266 | 10/1998 |
| DE | 19801492 | 10/1998 |
| DE | 19846742 | 4/2000 |
| DE | 19858172 | 6/2000 |
| DE | 10105315 | 6/2002 |
| DE | 10119452 | 11/2002 |
| DE | 10156469 | 6/2003 |
| DE | 10233601 | 2/2004 |
| DE | 10258071 | 6/2004 |
| DE | 102004001635 | 8/2005 |
| DE | 102005020569 | 11/2006 |
| DE | 102007059300 | 6/2009 |
| DE | 102008026237 | 12/2009 |
| DE | 102008030942 | 1/2010 |
| EP | 0117050 | 8/1984 |
| EP | 0135991 | 4/1985 |
| EP | 0258777 | 3/1988 |
| EP | 0267584 | 5/1988 |
| EP | 0303436 | 2/1989 |
| EP | 0308815 | 3/1989 |
| EP | 0369383 | 5/1990 |
| EP | 0417865 | 3/1991 |
| EP | 0421558 | 4/1991 |
| EP | 0437291 | 7/1991 |
| EP | 0442579 | 8/1991 |
| EP | 0482114 | 4/1992 |
| EP | 0617975 | 10/1994 |
| EP | 1380317 | 1/2004 |
| EP | 1343557 | 9/2004 |
| EP | 2055227 | 5/2009 |
| EP | 2090330 | 8/2009 |
| FR | 2768057 | 3/1999 |
| FR | 2772278 | 6/1999 |
| JP | 4538665 | 9/2010 |
| WO | WO0007907 | 7/1990 |
| WO | WO9733513 | 9/1997 |
| WO | WO0205710 | 1/2002 |
| WO | WO0220083 | 3/2002 |
| WO | WO02/36193 | 5/2002 |
| WO | WO2004107953 | 12/2004 |

\* cited by examiner

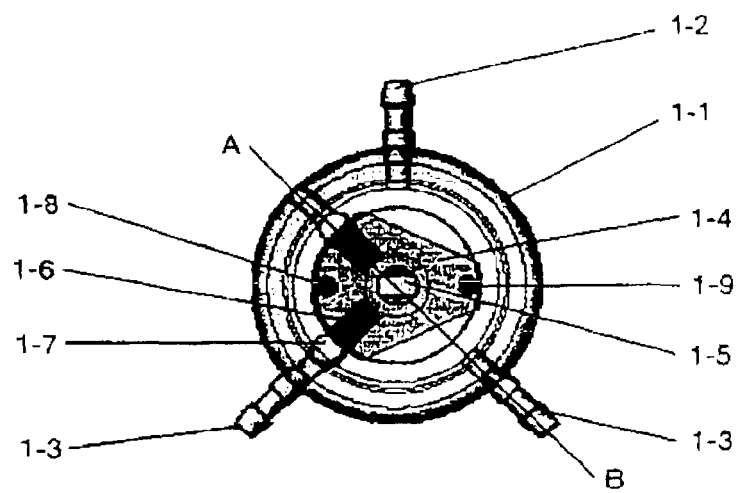
Fig. 1 Switching position 1 - discharge 1 closed, discharge 2 open
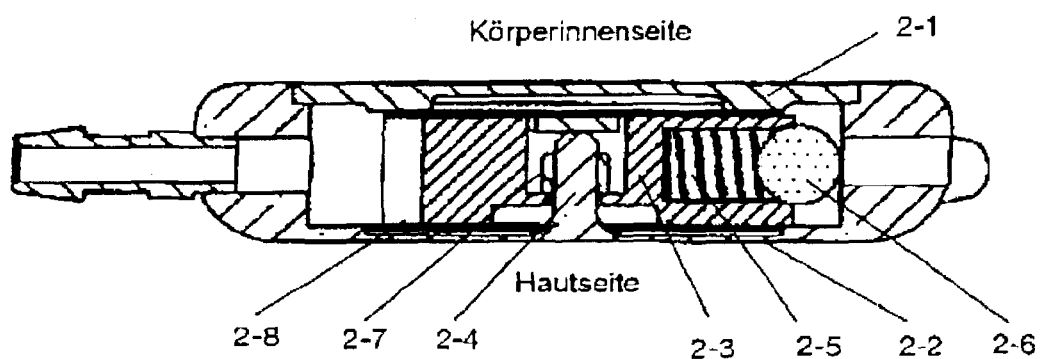
Fig. 2 Section A-B through the switch of Fig. 1

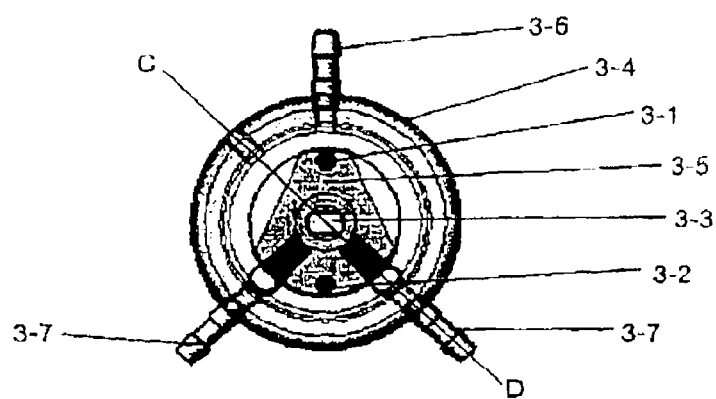
Fig. 3 Switching position 2 - discharge 1 closed, discharge 2 closed
Inner body side
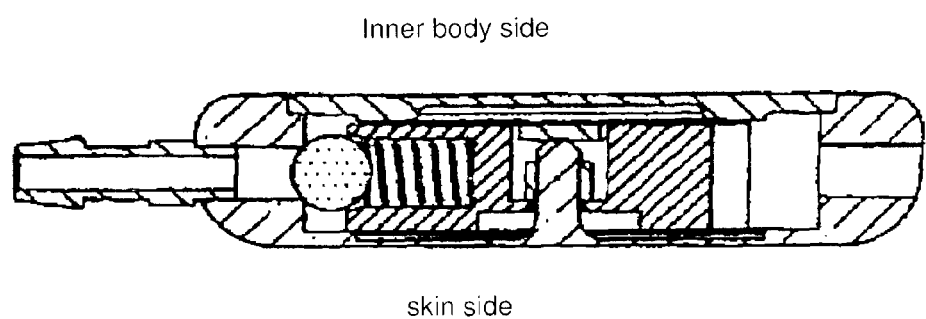
skin side
Fig 4 Section C-D in the switch in Fig. 3

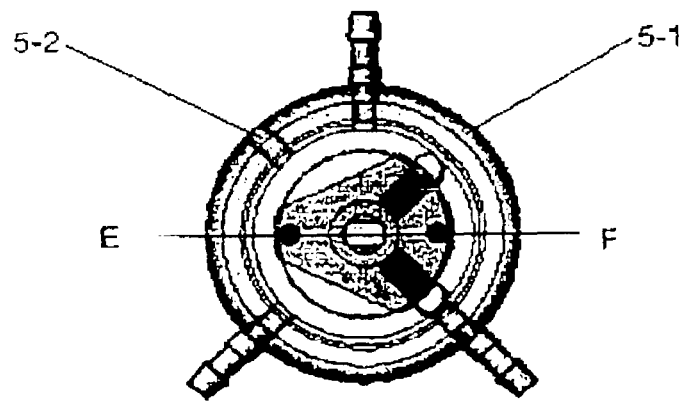
Fig. 5 Switching position 3 - discharge 1 open, discharge 2 closed
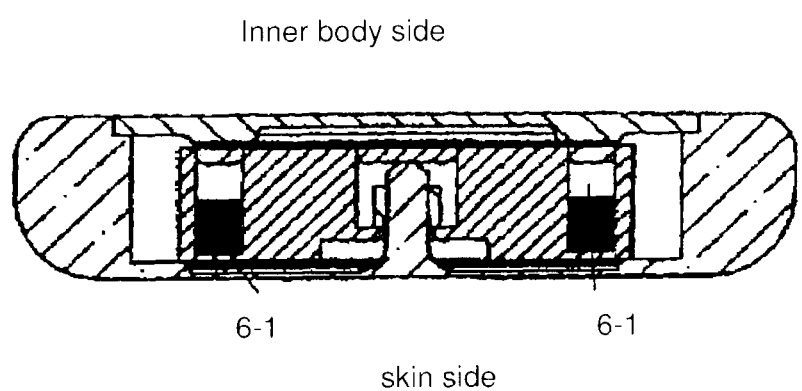
Fig. 6 Section E-F in switch of Fig. 5

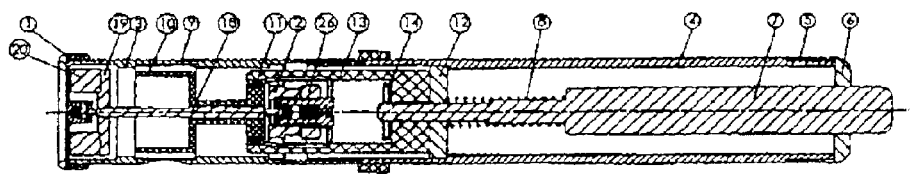
Fig. 7 Reference numbers 7-xx
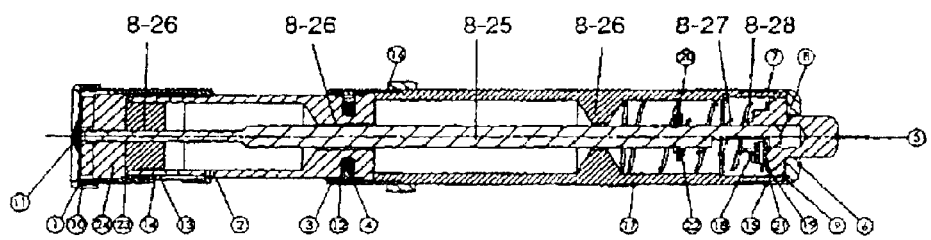
Fig. 8 Reference numbers 8-xx

CEREBROSPINAL FLUID DRAINAGE

CONTINUING APPLICATION DATA

This application is a Continuation of U.S. application Ser. No. 12/981,224, which is a Continuation-In-Part application of International Patent Application No. PCT/EP2009/004751, filed on Jul. 1, 2009, which claims priority from Federal Republic of Germany Patent Application No. 10 2008 030 942.7, filed on Jul. 2, 2008. International Patent Application No. PCT/EP2009/004751 was pending as of the filing date of this application. The United States was an elected state in International Patent Application No. PCT/EP2009/004751.

BACKGROUND

1. Technical Field

The present application relates to a percutaneously adjustable drainage system for cerebrospinal fluid.

2. Background Information

Background information is for informational purposes only and does not necessarily admit that subsequently mentioned information and publications are prior art.

Initial Situation:

Cerebrospinal fluid drainage is required and/or desired for example for hemorrhages resulting from a head injury or for cerebral hemorrhages resulting from an aneurysm. Cerebrospinal fluid drainage is also frequently used for equalizing the pressure or decreasing the pressure in hydrocephalus patients.

Cerebrospinal fluid drainage influences the pressure conditions in the intracranial cavity of the patient and prevents, minimizes, and/or restricts any damage to the brain from excessive intracranial pressures.

Internal and external drainage are used for pressure equalization/reduction. The cerebral fluid must only or should flow away in a controlled or substantially controlled manner. An uncontrolled discharge is just as dangerous as an excessive pressure. The discharge of the cerebrospinal fluid is controlled by means of a valve.

For internal drainage an artificial connection is produced between the ventricles of the brain in the head and a drainage compartment, which is currently most often the abdomen. For the external drainage, the cerebral fluid is passed through a catheter outside the body.

Examples of suitable hydrocephalus valves are described in DE 102004015500 A1, DE102004001635 A1, DE 69808558 T2, DE19643782 C1, DE19535637 C2, DE10358145 A1, DE10258071 A1, DE 10105315 A1, DE 4401422 B4, DE 4307387 C2. DE 4130601 A1, DE26202 A1, EP 1 575 654 A1, EP1 343 557 B1, EP888 595 B1, EP614 673 A3.

Problematic Issues:

External drainages have a rapidly increasing risk of infection as a function of the duration of the treatment. In view of the extremely high risk of infection, an external drainage can no longer be justified after seven to ten days.

Internal drainage by means of a shunt system has a high risk of blockage by blood components in the cerebrospinal fluid.

OBJECT OR OBJECTS

An object of the present application is to take account of the clinical situations and to minimize stress to the patient.

SUMMARY

This is achieved with the features of the asserted patent claims. The present application in one possible embodiment addresses the problem of enabling the discharge to be adjusted.

The blockage problem is solved according to the present application by providing at least one further second discharge pipe and/or a second supply pipe on the drainage valve for the cerebrospinal fluid. Still more discharge pipes and/or supply pipes can also be considered in addition to the second discharge pipe and/or discharge pipe.

The discharge pipes according to the present application can lead to different or the same parts of the body that receive the drained cerebrospinal fluid. The different supply pipes can join the same or other points in the cranial cavity.

In one possible embodiment of the present application, the usual parts such as the superior vena cava and/or the abdominal cavity can be considered as body parts for receiving cerebrospinal fluid. Other body parts can also be considered for receiving the cerebrospinal fluid. Optionally, an internal drainage can also be linked with an external drainage. According to the present application, a plurality of lines from the valve then lead to body parts and to an externally positioned point, where the cerebrospinal fluid is collected.

For the points in the cranial cavity where the drainage begins, the same applies as for the body parts or the external point for receiving the cerebrospinal fluid. For receiving the cerebrospinal fluid, a place can be selected from which a pipe leads to the valve. The discharge pipes according to the present application can be combined with a plurality of supply pipes on the valve. However, a plurality of discharge pipes can also be combined with a common supply pipe or a plurality of supply pipes can be combined with a common discharge pipe.

According to the present application, in one possible embodiment not only a pressure control but also a switch is provided in the valve. In the case where a pressure increase indicates a danger of blockage in a drainage pipe, then there is in one possible embodiment an automatic switch over to another drainage pipe. Optionally, the various pipes can also be partially open or closed, such that the various supply pipes or discharge pipes are run in parallel or substantially parallel.

However, the present application can also be utilized to counteract an initial occurrence of blood in the cerebrospinal fluid with an external drainage until the patient is stabilized and to switch over to an internal drainage when the blood occurrence halts.

The switch and the pressure gauge are optionally realized in a common component. This can be realized for example with a spring-loaded valve that on reaching a defined pressure opens or closes or partially opens or partially closes. Valves of this type can be resilient membranes or spring-loaded balls or spring-loaded valve caps.

Separate mechanical caps or sliders or spheres can optionally also be provided, also then when the pressure is measured mechanically with the above described spring-loaded spheres or valve caps or when the impulse for a switch over is given by the pressure measurement. The operative connection can be purely mechanical or electric or mechanical/electric. For electrical actuation a battery is provided in the valve for the power supply.

The actuation can be automatic or also semi-automatic or can be effected manually. For manual control exclusively, the switch over and the pressure measurement are done by hand. For semi-automatic control according to the present application, the pressure is measured automatically and a significant pressure change raises an alert with the medical staff, who then carry out the switch over.

In at least one possible embodiment of the present application, the pipes provided according to the present application which are not actually needed and/or required for a cerebrospinal drainage, are closed. In at least one possible embodiment, this is done automatically or substantially automatically by using a slider as the valve, in that the slider opens supply pipes and/or discharge pipes and closes other supply pipes and/or discharge pipes. Another design of the valve has a combination of elements or valve parts that perform the various functions and together form the valve. Elements with diverse closing and opening functions can be included in them.

In at least one possible embodiment of the present occasion, sliders may be used for the valve according to the present application, which are rotatably positioned in the valve housing. The rotatably positioned sliders are called rotary slides. Rotating them opens and/or closes openings in the housing. According to the present application, the term "rotating" includes each rotational direction and also rotational movements of a few degrees about the rotational axis. Such rotational movements can also be called pivoting.

The openings are equivalent to connections of the supply pipes and/or discharge pipes. The valves according to the present application optionally possess more openings than are normally required and/or desired. The unneeded openings are sealed with blind plugs and opened when needed and/or desired.

Optionally, a connection between the various openings is produced in that the slider is equipped with openings that, when two openings are connected, one of the openings leads to the other opening and when adjusted, at least one of the openings is sealed again. These openings can be formed by drilled holes that traverse the slider. The drilled holes can run through the rotatably movable slider in the radial direction and/or in the circumferential direction and/or in the axial direction. The holes can also run as slits on the periphery of the slider. The slits can extend in the circumferential direction and/or in the radial direction and/or in the axial direction of the rotary slider. The slides can be any shape with a round and/or rectangular and/or straight cross section. In the context of the present application, each flat portion on the periphery of the slider is already a slit. The holes can be inserted afterwards into a prefabricated rotary slider subassembly or taken into account from the beginning when manufacturing the slider.

Optionally, a connection exists between the various openings in that in the inner side of the valve housing are found holes that extend with respect to the rotary slider in the peripheral direction and/or in the axial direction.

Holes are optionally provided in both the housing as well as in the rotary slider.

Considering the low pressures that are encountered with a limited clearance between the rotary slider and the inner side of the housing, a gasket is unnecessary and/or not desired. The clearance is defined as the distance between the moving sealing surface of the rotary slider and the fixed sealing surface belonging to the valve housing. An adequate sealing effect can already be based on a clearance of at most 0.5 millimeters, in one possible embodiment at most 0.3 millimeters.

Optionally, instead of a small clearance or in addition to a small clearance, one more valve ball seal is provided for the opening to be sealed. In this case the seals are also like those on valves that are described in the abovementioned printed publications. They are spring-loaded balls made of ruby, sapphire, tantalum, titanium or the like. The remaining parts are in one possible embodiment made of titanium or tantalum. The balls are spring-loaded. The spring is in one possible embodiment embedded in the rotary slider. That means that in the rotary slider is a bore, whose inner diameter is matched to the outer diameter of the spring, such that the spring is in fact guided in the bore, but when pressed together it is not frictionally blocked in the bore.

In the sealing function, the balled is pressed into the relevant opening in the valve housing. The ball can press onto a sharp edge, but it is better for the ball and for the performance of the seal that there is at least a chamfer on the opening which at least acts like a type of valve seat.

The smaller the ball, the further the ball penetrates into the opening in the valve housing and therefore the higher is the resistance against a shift of the rotary slider. The diameter of the ball in relation to the relevant opening is in one possible embodiment at least thirty percent greater, in one possible embodiment at least fifty percent greater and most in one possible embodiment at least seventy percent greater.

Optionally, instead of the valve ball seal in the openings of the discharge pipes, a valve ball seal is also provided on the openings of the supply pipes. Valve ball closures can also be provided for all and/or substantially all and/or most openings. Different seals can also be combined with one another. The valve ball seals on the supply pipes are designed to maintain the pressure of the cerebrospinal fluid at a desired level. In contrast to the valve ball seals on the discharge pipes, an adequate flow cross section is then provided to the supply pipes for the cerebrospinal fluid, which overcomes the pressure on the valve ball and flows into the valve housing; from there it flows out through an open discharge pipe.

Optionally, the rotary slider is percutaneously adjusted with the help of magnets, in one possible embodiment as in the manner described in EP03767779.6-2310. Here a self-activating brake can also be used, as is described in the published document. At least one possible embodiment of the present application, the self-activating brake may be used when no other braking action is provided. Another braking action results with the above described ball seals and with the rolling resistance or rotational resistance resulting from them. A self-activating brake may then be unnecessary and are not desired.

By using the present application, the treatment is significantly simplified by the simultaneous and/or substantially simultaneous implantation of the direct discharge pipe and the shunt system;

the risk of infection to the patient is significantly minimized, it allows the doctor to make non-invasive individual adjustments and, depending on the course of therapy, makes possible repeated adjustments there is reduced physical stress by reducing the operations, accompanied by a reduction in the treatment costs significantly more treatment possibilities are made available by changing the cerebrospinal fluid drainage.

The present application respects the requirements for routine clinical use due to the availability of a plurality of switching states that can be non-invasively and percutaneously adjusted by the doctor and adapted to the therapeutic situations.

Thus, one switch position can completely or substantially completely close the discharge pipe, one switch position can open the discharge pipe for immediate and/or substantially immediate drainage and a second switch position can enable the discharge through an implanted valve.

The consequence for the patients is firstly a reduction in the invasive interventions by a subsequent adjustment of the switching state and the associated discharge.

Mode of Operation and Construction:

The two-way discharge switch works independently of the body position of the patient.

The switching state is obtained according to the present application with an adjustable mechanism.

This principle can be realized in various ways.

The movable closing element is in one possible embodiment combined with a movable and adjustable precision non-return valve. At least one possible embodiment of the present application, this results in an advantageous design freedom.

The closing element is in one possible embodiment somewhat larger than the precision non-return valve. In addition, the weight of the closing element can be further influenced by choosing a material with a higher density.

Another embodiment comprises in the design with a second ball unit that is incorporated in the closing element. The ball is in one possible embodiment made of a heavy metallic material with a high density (in one possible embodiment, a tantalum may be used here).

According to the present application, one or two spring-loaded balls of the precision non-return valve in the corresponding switching position of the closing element press against the openings of the discharge pipes. The balls are located in a guide that is formed by cylindrical bores.

Optionally, the closing element is shaped like a disc, a rod, a ring, a cap or a bell. This design makes available additional design possibilities for the closing element. The disc can utilize the largest dimension of the switch housing.

According to the present application, the disc, in spite of its low thickness, can easily possess the desired weight because of its large dimension. The same is true for a circular design.

In at least one possible embodiment of the present application, the disc and of the ring can optionally be combined in the shape of a cap or a bell.

The cap form in one possible embodiment has a cylindrical casing and a flat, disc-shaped cover. The bell form optionally has a conical casing. A suitable material is titanium; in one possible embodiment, tantalum is a material for a compact design.

The closing element, inventively designed as a disc, a rod, a ring, a cap or a bell, is in one possible embodiment pivotably movably located in the switch housing. In at least one possible embodiment, the pivotably movable configuration forms a guide for the closing element as friction, which acts against a precise or substantially precise mode of operation of the switch, can be minimized for the movements induced by a change in posture. The position of the pivot axis is in one possible embodiment chosen such that the closing element presses centrally on the precision non-return valve.

In the pivotable movement of the closing element, the closing element should depart as little as possible from the vertical or the substantially vertical. In addition, the pivot shaft is arranged such that it has a greatest possible distance from the vertical or substantially vertical going from the ball used in the precision non-return valve. The pivot shaft can be firmly connected with the closing element and pivotably mounted in the valve housing. In accordance with at least one possible embodiment, the fixation of the pivotable closing element on the shaft may be advantageous.

The operative connection with the precision non-return valve constructed as a ball or flap is formed in that the closing element slidingly presses against the precision non-return valve.

The operative connection with the adjustment mechanism depends on the design of the adjustment mechanism. A rotating device or pivoting device, which is equipped with a sliding surface, is in one possible embodiment provided as the adjustment mechanism. The effects of an adjustment depend on the design of the closing element.

The closing element can alternatively be combined through a guide by means of a spring in the form of a spiral spring, wire spring or leaf spring. The spring according to the present application can have any cross section. Circular and rectangular shapes are possible. In at least one possible embodiment, a spring with a leaf-shaped or wire-shaped cross section maybe desired. For the fixation, a welded or soldered connection as well as other connections are suitable. Moreover, other mechanical connections such as clamp connections and plug connections also come into consideration.

The curved path of the closing element in one possible embodiment runs around the pivotably movable or rotatably movable part. The circumferential angle to the pivotably movable or rotatably movable part comprises at least three hundred degrees.

When using a rod as the closing element, it is favorable if a large surface is available for contact between the closing element and precision non-return valve. If this large surface contact is not provided then a metal sheet can be fastened to the relevant end of the rod. The metal sheet is optionally welded on or soldered on or fastened in another way.

The closing element is secured in the relevant rotational position. Various systems are available for this. Purely mechanical brakes can be used. A self-activating brake is in one possible embodiment used which is formed in that the closing element is frictionally clamped in the switching housing after each adjustment movement. For another adjustment, the switching housing is deformed in such a way that the switching housing with its frictional surfaces lifts off from the corresponding frictional surface of the closing element. The required and/or desired deformation occurs due to pressure.

In at least one possible embodiment of the present application, the frictional surfaces may be located on the sides of the switching housing. According to an older suggestion, the frictional surfaces are located in other places, namely directly on the base or lid of the switching housing or an element of the adjustment device that cooperates with the base or lid. By pressing the base or lid, the adjustment device becomes available for an adjustment. On releasing the pressed base or lid, the base or lid returns to its original shape, and the friction-tight connection between the lid or the base and the closing element is re-established.

The closing element is secured in the respective rotational position by means of another known concept with the help of magnets. For this, magnets/permanent magnets can be located on the adjustment device and/or on the inner side of the housing. The magnets form an element of a locking device. The locking device can comprise other movable parts that, because of the magnetic field, engage into locking holes or into toothing. However, the locking can be disengaged by using stronger magnets.

The use of reactive materials for the magnets, e.g. steel or also magnetic material, may be possible.

Moreover, it is convenient to choose the frictional surfaces such that there results a particularly strong or substantially particularly strong self-locking action. For this, according to the present application, a minimum distance of the frictional surfaces to the rotational axis or pivot axis of the pivotably movable or rotatably movable elements is provided. The frictional surfaces are in one possible embodiment located as far away as possible from the switching housing center on the outer edge of the pivotably movable or rotatably movable element of the closing element.

According to the present application, small pin magnets are in one possible embodiment used as the magnets. The small magnets also contribute to the small dimensions of the switching housing, as they are a subject matter of the present application.

Adjustment Device:

The two-way discharge switch can be very easily adjusted to match the changed conditions that are required and/or desired on therapeutic grounds.

The switch adjustment is extremely secure.

This security is inventively realized by means of a magnetically activated disc spring that is integrated into the housing and which locks the closing element in position and prevents, restricts, and/or minimizes any unwanted adjustment.

The adjustment device for the discharge switch according to the present application can likewise be designed with extremely small dimensions. According to the present application, use is made of a reduced diameter and a particular and/or substantially particular shape of the adjustment device, namely in the design of a pen-shape, similar to a ballpoint pen. This allows the adjustment device to be handled like a pen or ballpoint pen. Such instruments can, in practice, be carried in a breast pocket. At the same time the mechanism of a ballpoint pen is utilized in order to utilize the magnets provided in the head of the instrument for measuring the preset switching state, or even for setting the switching state. A similar mechanism is used as in the ballpoint pen for retracting or extending the lead. It is utilized here to friction lock or to release the magnetic drum with the adjustment device.

The pen-shaped adjustment device according to the present application optionally possesses on the front end a cap, with which the adjustment device is fixed. By loosely placing the adjustment device onto the discharge switch the magnets automatically center themselves.

After the adjustment device has been centered, the discharge switch is in one possible embodiment elastically deformed. The deformation should be made by a controlled pressing of the adjustment device on the implanted discharge switch. According to the present application, the deformation causes the pivotably movable or rotationally movable part of the switch housing to lift up. Consequently the friction decreases. It decreases to a minimum; this is called a neutralization of the friction.

After neutralization of the friction, the pivoting or rotating part on the switch side can be easily moved to the magnet positions of the previously incorporated magnets of the adjustment device or can assume its position.

The above-discussed embodiments of the present invention will be described further herein below. When the word "invention" or "embodiment of the invention" is used in this specification, the word "invention" or "embodiment of the invention" includes "inventions" or "embodiments of the invention", that is the plural of "invention" or "embodiment of the invention". By stating "invention" or "embodiment of the invention", the Applicant does not in any way admit that the present application does not include more than one patentably and non-obviously distinct invention, and maintains that this application may include more than one patentably and non-obviously distinct invention. The Applicant hereby asserts that the disclosure of this application may include more than one invention, and, in the event that there is more than one invention, that these inventions may be patentable and non-obvious one with respect to the other.

BRIEF DESCRIPTION OF THE DRAWINGS

The FIGS. 1 to 6 illustrate the same discharge switch in the various switching states;

FIG. 7 shows one possible embodiment of a measuring instrument;

FIG. 8 shows another embodiment of an adjustment pin

DESCRIPTION OF EMBODIMENT OR EMBODIMENTS

Figure 9:
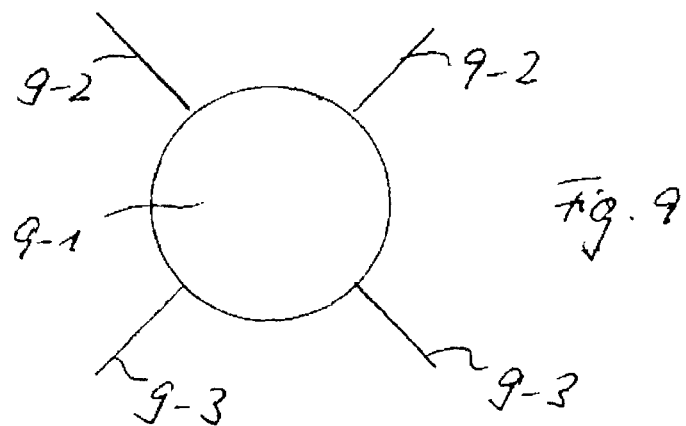
FIG. 9 shows one possible embodiment of a valve according to the present application corresponding to one of the FIGS. 1 to 6.

In the drawing of FIG. 1 an embodiment of the present application is illustrated in the switch position 1 (discharge 1 closed, discharge 2 open).

In the drawing of FIG. 2 is illustrated the view of the section A-B of the switch of FIG. 1.

The two-way discharge switch comprises a solid metallic housing 1-1, a lid 1-2, a base 2-2 as well as an inlet port 1-2 and outlet port 1-3. Moreover, in the embodiment, the 2-way discharge switch possesses a closing element 1-4/2-3 that is mounted on the shaft 1-5/2-4, a spring system 1-6/2-5 with a ball 1-7/2-6 for the precision non-return valve and a locking device 2-7. The two-way discharge switch is located in a tube that is implanted in a patient for cerebrospinal fluid drainage. The two-way discharge switch has three switching states. Switching state 1 closes discharge 1 and opens discharge 2, switching state 2 closes both discharges 1 and 2, and switching state 3 closes discharge 2 and opens discharge 1. In the switching state 1 and 3, cerebrospinal fluid flows through the two-way discharge switch.

The two-way discharge switch in one possible embodiment comprises a solid titanium housing 1-1. The housing is circular in shape and is closed by a lid 2-1.

The balls 1-7/2-6 of the precision non-return valve are made of sapphire, ruby, a ceramic material or titanium. In principle all or substantially all or most biocompatible materials with a highest possible density are suitable.

Two magnets 1-8/1-9 with opposite polarity are placed into the closing element. The closing element 1-4 is held on a shaft 1-5. The shaft 1-5 is located on the lid 2-2. In relation to the housing, the lid is convex. The closing element 1-4 is tightened with a screw on the shaft 1-5 against the lid such that a contact pressure of the closing element on the lid results in a friction locked connection of the closing element with the lid, and the closing element is prevented, restricted, and/or minimized from an unwanted rotation 2-8 (friction surface). The friction lock will remain until an adjustment (mentioned below) is made. The level of the friction lock is chosen such that no unwanted displacement of the closing element occurs, even by unforeseen magnetic fields.

The friction lock is produced on the outer edges of the closing element. This results from the outwardly directed curvature of the lid and due to the fact that the surface of the corresponding closing element is flat.

Pressing on the lid 2-2 causes the lid to deform elastically. The lid becomes flatter or even assumes an opposite curvature.

Thus, the outer edges of the closing element on the friction surface 2-8 are released from the lid and the closing element can be rotated with magnetic force.

The thickness of the lid is in one possible embodiment 0.1 to 0.2 millimeters, in other embodiments it is up to 0.5 millimeters. The deformation associated with the elastic deflection is in one possible embodiment 0.01 to about 0.1 millimeters, in other embodiments up to twice the lid thickness. The greater the lid is prestressed, the more one has to press or should press from outside in order to lift up the closing element from the lid and to release the locking of the closing element on the lid.

In FIG. 2, the skin side is below in the drawing and the interior of the body is above in the drawing. If a pressure is mechanically exerted from the outside through the skin on the lid 2-2, depending on the force, the lid 2-2 is deformed/curved inwardly and the shaft 2-4 is pushed downward to the lid 2-1. As a result, a gap is opened on the friction surface 2-8, the whole closing element lifts off the lid. The elastic bias of the lid 2-2 and the frictional forces at the position 2-8 are thereby neutralized. A gap is then created at the position 2-8, and the closing element can rotate freely. If the external load is removed again, the outer lid 2-2 returns to its initial position and generates the elastic bias between contact points on the friction surface 2-8. The closing element is again clamped in the housing, and no rotation is possible.

In the drawing of FIG. 3 an embodiment of the present application is illustrated in the switch position 2 (discharge 1 closed, discharge 2 closed). In the drawing of FIG. 4 the view of the section C-D of the switch of FIG. 3 is illustrated.

In FIG. 3 the closing element is illustrated in the center position. A rotation of approximately ±ninety degrees brings the closing element into the respective maximum position.

The two magnets 3-1 and 3-2 are arranged such that an externally applied magnetic field can produce a maximum torque.

In other words, the distance between the two magnets in the embodiment is seven millimeters. In another embodiment it is eight millimeters and in additional embodiments it can be up to twenty millimeters. In practical terms, this difference is determined on the basis of the external dimensions of the housing. The circular housing in one possible embodiment has a diameter of fourteen millimeters, in other embodiments a diameter of up to nineteen millimeters and in additional embodiments diameters of up to thirty-one millimeters, and is shaped ergonomically, such that on the one hand the position of the two-way discharge switch can be easily felt from outside, while on the other hand the tissue that lies on top of the two-way discharge switch is not damaged. Sharp edges are thereby avoiding, restricted, and/or minimized.

The shaft 3-3 in one possible embodiment has a diameter of 0.3 millimeters and can optionally have a tip on the top and bottom to minimize the bearing forces. As a result of the construction described above, the closing element can rotate if or only if the lid is pressed and the closing element can thereby rotate freely. In this position, a specific magnetic field must also be or should be located externally to securely initiate a rotation. If the load is then removed from the lid, the position of the closing element is fixed by elastic clamping.

In at least one possible embodiment of the present application, the placement of the magnets 3-1 and 3-2 as far apart from each other as possible such that the lowest possible magnetic forces can achieve the highest possible adjustment moments. In one possible embodiment, the fabrication of the housing 3-4 and the closing element 3-5 and the fabrication of the other components from titanium may comprise a bearing play such that exact or substantially exact fits may be achieved, and undesirable play and undesirably high friction can be systematically avoided, restricted, and/or minimized.

The height of the two-way discharge switch is approximately 4.5 millimeters. Significantly lower heights are not necessarily desirable or may not be desired, if even possible, because it should not be too difficult to locate the valve by palpation.

The housing 3-4 is equipped with a connecting piece 3-6 and two outlet pieces 3-7. The outer end of the connecting pieces is shaped as a connection for the flexible hose. On the inside, the connection pieces protrude through the wall of the housing into the interior of the housing. The outlet pieces are mounted in the same way as the connection pieces.

The cerebrospinal fluid arriving in the upper connecting piece 3-6 flows downwards into an outlet opening 3-7 and into a subsequent part of the flexible hose (not shown).

In the drawing of FIG. 5 an embodiment of the present application is illustrated in the switch position 3 (discharge 1 open, discharge 2 closed).

In the drawing of FIG. 6 is illustrated the view of the section E-F of the switch of FIG. 5.

The housing 5-1 possesses (for X-ray detection) an additional bore 5-2 that remains inoperative and is sealed with a stopper (not shown).

In at least one possible embodiment of the present application, the magnets 6-1 may be cylindrical in shape, have a diameter of approximately one millimeter and are about 1.2 millimeters in height.

Special measurement and adjustment pins have been developed for adjusting the two-way discharge switch. An embodiment of such a pin is illustrated in FIGS. 7 and 8. The illustration is of larger size than the embodiment, but not as large as in FIGS. 1 to 6. To arrive at the correct relationship between the dimensions of the two-way discharge switch and the dimensions of the pin as the adjustment device, it is recommended to look at the pin in an appropriate enlargement together with the two-way discharge switch.

In a to-scale illustration, all or substantially all or most of the details would be so small that they would no longer be discernible.

Measuring Instrument FIG. 7

A thin-walled small tube from two parts of the housing 7-3 and 7-4 with a diameter of approximately twelve millimeters is sealed at one end by a stopper 7-6. On the other side, is installed a measurement mechanism mounted on a needle bearing. The mechanism possesses: a measurement drum 7-10, on the surface of which is applied a graduated scale, the drum being connected with the shaft 7-18 that is mounted in the bearing bushing 7-13 at the points 7-11. The bearing bushing 7-13 is introduced into the small tube 7-4 such that it cannot be displaced or rotated by the brake 7-2 and 7-26. On the side of the small tube that is not closed, a movable pin 7-7 is inserted into the small tube, and is pushed outward by a spring force of the spring 7-8. The spring 7-8 is supported on the locking plate 7-12 of the bearing bushing and presses the ring 7-14 against the bearing bushing 7-13. Magnets 7-20 are introduced into the cylinder 7-19. The external pole on the one magnet is positive and on the other magnet it is negative. The distance between the magnets is approximately equal to the distance between the magnets inside the two-way discharge switch, likewise the diameter.

Actuating the pins 7-7 releases the bearing bushing 7-13 from the locking plate 7-12, and the magnets 7-20 can obey the magnetic field of the discharge switch. After positioning the magnet of the measuring pin over the magnets of the discharge switch, the switching position can be read off the graduated scale of the measurement drum 7-10 through the viewing window 7-9. The corresponding adjustment pressure of the two-way discharge switch can now be easily read off in the window 7-9. This construction essentially guarantees and/or promotes a reliable, reproducible measurement at all or substantially all or most times. By fixing the reference value a few tenths of a millimeter away from the head or only a few tenths of a millimeter away from the head, it is no longer possible to rotate the pin or to remove it from the patient's head. The adjustment is immediately or substantially immediately locked.

Adjustment Instrument FIG. 8

FIG. 8 shows another embodiment of an adjustment pin. The external dimensions are approximately the same as those of an ordinary ballpoint pen, i.e. the small tube has an outside diameter of in one possible embodiment twelve millimeters and a length of approximately ten centimeters. The adjustment wheel 8-2 is in one possible embodiment fixed to the shaft 8-25. A rotation of this wheel causes a rotation of the shaft. On the lower end of the shaft 8-25, two cylindrical magnets 8-24 are introduced into the shaft. As in the two-way discharge switch, these magnets have different polarities. The south pole of one of the magnets is on the bottom, and on the other magnet the north pole is on the bottom. The position of both magnets on the shaft corresponds to the position of the graduated scale that can be read off through the viewing window 8-13. This graduated scale is also permanently or substantially permanently connected with the shaft 8-25.

A plurality of bushings 8-26 act as a bearing for the shaft 8-25. The adjustment pin comprises two different springs: a strong spring 8-27 and an extremely weak spring 8-28. By pressing on the button 8-5, the shaft 8-8, which has a piston-like expanded portion in its lower region, is displaced downward against the spring force 8-28. The shaft 8-8 is thereby pushed downward against the spring force of the significantly weaker spring 8-27. The spring 8-28 is therefore significantly compressed, while in contrast the spring 8-27 is slightly compressed or only slightly compressed. The force of the shaft is transmitted to its lower tip, which in this application is designed to exert the force on the two-way discharge switch that is to be uncoupled. The diameter of the shaft at the tip should in one possible embodiment be approximately three millimeters, and the bottom end should be rounded in a dome shape. The cap 8-1 that is attached to the lower end of the pin protects the bearing as well as the magnets 8-24 that are installed in the shaft 8-8. The position of the magnets can be read through the window 8-13 on the graduated scale of a scale drum. The proposed construction makes it possible to keep the construction of the adjustment unit small without negatively affecting the safety and reliability of the adjustment. Therefore, for the first time, it becomes possible to realize such adjustment pins. The construction makes it possible to place the magnets as close as possible to the patient's skin. A precise or substantially precise and accurate or substantially accurate adjustment can be made by the simultaneous or substantially simultaneous application of pressure to the housing of the two-way discharge switch.

FIG. 9 shows a valve 9-1 according to the present application corresponding to one of the FIGS. 1 to 6. Two supply lines 9-2 lead to the valve 9-1. Two discharge lines 9-3 come off the valve 9-1. By switching, the cerebrospinal fluid can be fed from one discharge line 9-3 or from the other discharge line 9-3. It is important that a plurality of discharge lines is assigned to a plurality of supply lines. In other embodiments, even more supply lines and/or discharge lines are provided. Moreover, in other embodiments the cerebrospinal fluid can be distributed to a plurality of discharge lines and the distribution can be changed by switching. Similarly, in other embodiments the supply of cerebrospinal fluid can be changed by switching.

Figure 10:
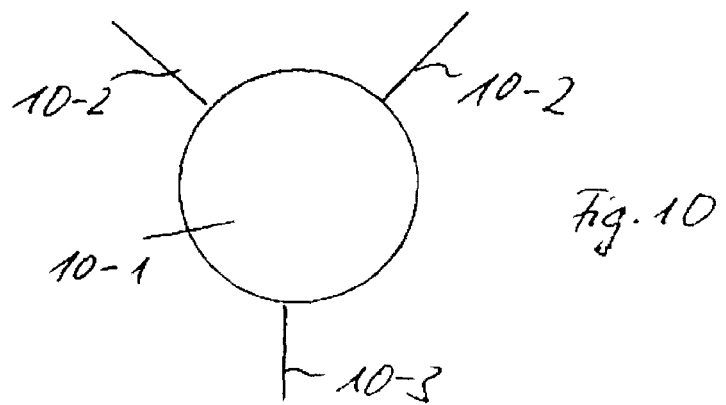
FIG. 10 shows another possible embodiment of a valve according to the present application.

FIG. 10 differs from FIG. 9 in that one discharge line 10-3 is provided for two supply lines 10-2. Switching the valve 10-1 680 serves to redirect from one supply line to the other and the other way round. In other embodiments, both supply lines act on the one discharge line and the distribution of the amount of cerebrospinal fluid flowing to the supply lines can be changed by switching. In other embodiments, the number of supply lines is greater.

Figure 11:
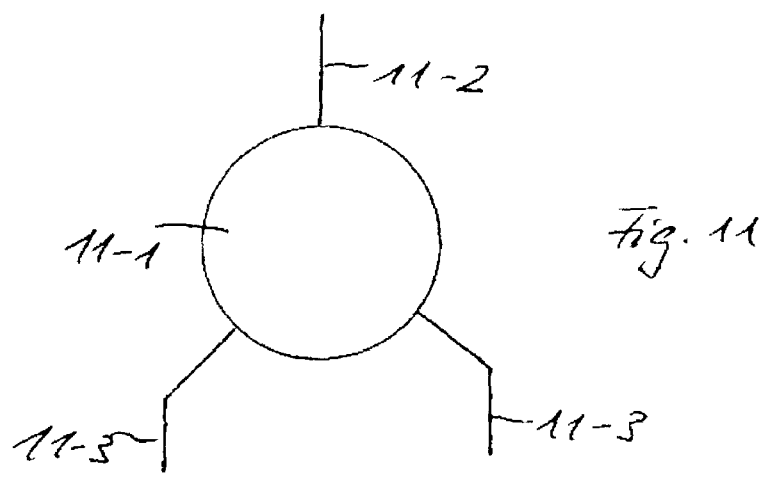
FIG. 11 shows yet another possible embodiment of a valve according to the present application.

FIG. 11 differs from FIG. 9 in that one supply line 11-2 is provided for two discharge lines 11-3. Switching the valve 11-1 serves to redirect from one discharge line to the other and the other way round. In other embodiments, both discharge lines act together and the distribution of the amount of cerebrospinal fluid into the discharge lines can be changed by switching.

In other embodiments, the number of discharge lines is greater.

According to the present application, a switch or valve is provided for the individual adjustment of drainage in the treatment of patients needing cerebrospinal fluid drainage, offering several drainage paths 1, 2 and drainage options and requiring post-operative and non-invasive switching of the drainage paths.

One feature or aspect of an embodiment is believed at the time of the filing of this patent application to possibly reside broadly in a device for draining cerebrospinal fluid comprising a supply tube and a discharge tube, wherein the supply tube takes up cerebrospinal fluid at a place in the cranial cavity and supplies a valve and the valve supplies the cerebrospinal fluid to a discharge tube, wherein at least one second supply tube and/or at least one second discharge tube is provided, wherein a switchable distributor for the cerebrospinal fluid is provided between the supply tubes and the discharge tubes.

Another feature or aspect of an embodiment is believed at the time of the filing of this patent application to possibly reside broadly in the device, wherein a) the various supply tubes take up the cerebrospinal fluid at one or more places and/or b) the various discharge tubes discharge the cerebrospinal fluid to one or more parts of the body and/or discharge to an external drainage place and/or c) a slider is used as the distributor with a closing element located therein, in one possible embodiment with a rotary slider, wherein the rotary slider possesses openings for controlling and/or distributing cerebrospinal fluid which extend in the peripheral direction and/or in the radial direction and/or in the axial direction in the slider and/or d) at the same time the distributor is designed as a valve, wherein the valve or distributor is equipped with a housing, wherein openings for distributing cerebrospinal fluids are located in the housing which, in relation to the rotating slider, extend in the peripheral direction and/or in the radial direction and/or in the axial direction, wherein the openings are totally or partially sealable.

Yet another feature or aspect of an embodiment is believed at the time of the filing of this patent application to possibly reside broadly in the device, comprising a rotary slider, in which a small clearance or at least a valve ball seal forms a seal on the openings to be sealed.

Still another feature or aspect of an embodiment is believed at the time of the filing of this patent application to possibly reside broadly in the device, wherein the rotary slider has the shape of a disc, a ring, a rod, a cap or a bell, and is arranged in a pivotably movable or rotatably movable manner in the housing.

A further feature or aspect of an embodiment is believed at the time of the filing of this patent application to possibly reside broadly in the device, wherein the valve ball of the valve ball seal reaches into the opening of the housing and forms an arrestor for the valve or distributor in the respective pivot position or rotational position.

Another feature or aspect of an embodiment is believed at the time of the filing of this patent application to possibly reside broadly in the device, wherein the valve ball seal is located wholly or partially inside a cavity of the ring, the rod, the cap or the bell which forms the rotary slider.

Yet another feature or aspect of an embodiment is believed at the time of the filing of this patent application to possibly reside broadly in the device, wherein the valve ball seal is located beside the ring, rod, cap or bell and that a spring passes through an opening in the ring, rod, cap or bell to the valve ball seal.

Still another feature or aspect of an embodiment is believed at the time of the filing of this patent application to possibly reside broadly in the device, wherein the guide is formed by a pivotably movable bearing or is a straight guide.

A further feature or aspect of an embodiment is believed at the time of the filing of this patent application to possibly reside broadly in the device, wherein a weight is attached to the valve ball seal, the weight being greater than that of the balls.

Another feature or aspect of an embodiment is believed at the time of the filing of this patent application to possibly reside broadly in the device, wherein the valve or distributor is at least partially made of ruby or sapphire or tantalum or titanium.

Yet another feature or aspect of an embodiment is believed at the time of the filing of this patent application to possibly reside broadly in the device, comprising a discoidal shape of the housing, wherein the closing element is arranged at a sufficient distance from the housing wall or from the housing base or housing cover for its movement in the housing and at a sufficient distance from the fixtures in the housing for movement.

Still another feature or aspect of an embodiment is believed at the time of the filing of this patent application to possibly reside broadly in the device, wherein the valve housing or distributor housing possesses at least one cover, and the disc, ring, rod, cap or bell that forms the closing element has a diameter that is smaller than the opening in the housing which corresponds to the cover.

A further feature or aspect of an embodiment is believed at the time of the filing of this patent application to possibly reside broadly in the device, wherein the spring is completely or partially fixed to the pivot shaft.

Another feature or aspect of an embodiment is believed at the time of the filing of this patent application to possibly reside broadly in the device, wherein the spring is designed as a spring wire or as a leaf spring.

Yet another feature or aspect of an embodiment is believed at the time of the filing of this patent application to possibly reside broadly in the device, where the spring is equipped with an adjustment device.

Still another feature or aspect of an embodiment is believed at the time of the filing of this patent application to possibly reside broadly in the device, wherein the adjustment device possesses a pivotably movable or rotatably movable element that is moved by means of magnets from the exterior by pivoting or rotating, such that the closing element or the spring is wound up or released.

A further feature or aspect of an embodiment is believed at the time of the filing of this patent application to possibly reside broadly in the device, comprising an activatable brake that when activated prevents, restricts, and/or minimizes an unintended adjustment movement and when deactivated allows the adjustment movement.

One feature or aspect of an embodiment is believed at the time of the filing of this patent application to possibly reside broadly in the device, comprising a self-activating spring-loaded brake that is deactivated by releasing the spring pressure.

Another feature or aspect of an embodiment is believed at the time of the filing of this patent application to possibly reside broadly in the device, wherein: the housing is resilient and has friction surfaces that in the unstressed state of the housing are friction-locked on at least one part of the adjustment device and by pressing together the housing are raised up from the corresponding surfaces of the adjustment device; or a housing is equipped with a resilient cover that in the unstressed state remains friction-locked to at least one part of the adjustment device and under pressure is raised up from the corresponding surfaces of the adjustment device.

Yet another feature or aspect of an embodiment is believed at the time of the filing of this patent application to possibly reside broadly in the device, wherein the resilient housing or the cover:

in the locked position of the brake exhibits an outwardly curved initial shape and after being pressed together forms a reduced curvature or a flat surface or an inward curvature;

in the locked position of the brake exhibits a flat initial shape and after being pressed together exhibits an inward curvature;

in the locked position of the brake exhibits an inward curvature and after being pressed together forms a greater inward curvature, or the housing wall possesses an inwardly curved initial shape and undergoes a further inward curvature from the deformation.

Still another feature or aspect of an embodiment is believed at the time of the filing of this patent application to possibly reside broadly in the device, comprising the use of a rotatably or pivotably movable rotary slider that possesses friction surfaces for locking on the external edge.

A further feature or aspect of an embodiment is believed at the time of the filing of this patent application to possibly reside broadly in the device, comprising the use of a rotatably or pivotably movable rotary slider that is prestressed with the housing walls that can be pressed together or with the compressible cover.

Another feature or aspect of an embodiment is believed at the time of the filing of this patent application to possibly reside broadly in the device, comprising a deformation of the housing wall for prestressing to a degree that is equal to twice the wall thickness of the housing, in one possible embodiment up to 0.1 millimeters.

Yet another feature or aspect of an embodiment is believed at the time of the filing of this patent application to possibly reside broadly in the device, wherein a rotary slider is used that has a U-shaped cross section, such that the frictional locking occurs on the projecting edge of the U-shape.

Still another feature or aspect of an embodiment is believed at the time of the filing of this patent application to possibly reside broadly in the device, comprising the use of a pressable housing wall or a pressable cover with a thickness of up to 0.5 millimeters, in one possible embodiment with a thickness of up to 0.2 millimeters.

A further feature or aspect of an embodiment is believed at the time of the filing of this patent application to possibly reside broadly in the device, wherein the housing, in one possible embodiment the deformable wall of the housing, comprises a metal, in one possible embodiment of titanium or a titanium alloy.

One feature or aspect of an embodiment is believed at the time of the filing of this patent application to possibly reside broadly in the device, wherein an adjustment device is provided percutaneously, to which belongs a percutaneously pressable, rotatable part with adjusting magnets.

Another feature or aspect of an embodiment is believed at the time of the filing of this patent application to possibly reside broadly in the device, comprising a pressure control of the rotary slider.

Yet another feature or aspect of an embodiment is believed at the time of the filing of this patent application to possibly reside broadly in the device, comprising the use of spring members to indicate the pressure and the pressure limitation and/or the use of elongating measurement strips for measuring the pressure.

Still another feature or aspect of an embodiment is believed at the time of the filing of this patent application to possibly reside broadly in the device, comprising the use of magnets with a diameter of up to three millimeters, in one possible embodiment a diameter of up to one millimeter and a height of up to five millimeters, in one possible embodiment a height of up to two millimeters.

A further feature or aspect of an embodiment is believed at the time of the filing of this patent application to possibly reside broadly in the device, wherein the magnets in the externally lying adjustment device are at a distance from one another that deviates from the magnets in the internally lying adjustment device by at most three millimeters, in one possible embodiment by at most one millimeter and/or the magnets are distanced apart by at most twenty millimeters, in one possible embodiment by at most ten millimeters and in one possible embodiment by at most eight millimeters.

Another feature or aspect of an embodiment is believed at the time of the filing of this patent application to possibly reside broadly in the device, wherein the externally lying adjustment device is equipped with a measuring device for the adjustment movement.

Yet another feature or aspect of an embodiment is believed at the time of the filing of this patent application to possibly reside broadly in the device, wherein the measuring device is a pressure measurement device and/or a device for measuring rotation.

Still another feature or aspect of an embodiment is believed at the time of the filing of this patent application to possibly reside broadly in the device, wherein the externally lying adjustment device acts freely on the magnet position of the closing element and is adjustable and that the rotation position of the magnets can be read off externally.

A further feature or aspect of an embodiment is believed at the time of the filing of this patent application to possibly reside broadly in the device, wherein the internally lying adjustment device possesses a spring in the form of a metallic wire or sheet, whose cross section is in one possible embodiment circular or rectangular and whose diameter or thickness is up to 0.5 millimeters, in one possible embodiment up to 0.3 millimeters and in one possible embodiment up to 0.2 millimeters.

Another feature or aspect of an embodiment is believed at the time of the filing of this patent application to possibly reside broadly in the device, wherein the spring bar: is designed as a single-armed lever; or is designed as a two-armed lever, of which one lever arm presses against the adjustment plate and whose other lever arm presses against the valve ball or valve cap of the valve or distributor in operative connection.

Yet another feature or aspect of an embodiment is believed at the time of the filing of this patent application to possibly reside broadly in the device, wherein the spring bar is flexibly mounted and presses in a sliding contact against a cam disc of the closing element and/or presses in a sliding contact against the valve ball closure.

Still another feature or aspect of an embodiment is believed at the time of the filing of this patent application to possibly reside broadly in the device, wherein the valve or distributor has an external diameter of up to thirty-one millimeters, in one possible embodiment up to twenty millimeters and/or a height of up to ten millimeters, in one possible embodiment up to six millimeters.

A further feature or aspect of an embodiment is believed at the time of the filing of this patent application to possibly reside broadly in the device, wherein the weight is positively connected with the spring element to be adjusted.

One feature or aspect of an embodiment is believed at the time of the filing of this patent application to possibly reside broadly in the device, wherein: a) the various supply tubes take up the cerebrospinal fluid at one or more places and/or b) the various discharge tubes discharge the cerebrospinal fluid to one or more parts of the body and/or discharge to an external drainage place and/or c) a slider is used as the distributor with a closing element located therein, with a rotary slider, wherein the rotary slider possesses openings for controlling and/or distributing cerebrospinal fluid which extend in the peripheral direction and/or in the radial direction and/or in the axial direction in the slider and/or d) at the same time the distributor is designed as a valve, wherein the valve or distributor is equipped with a housing, wherein openings for distributing cerebrospinal fluids are located in the housing which, in relation to the rotating slider, extend in the peripheral direction and/or in the radial direction and/or in the axial direction, wherein the openings are totally or partially sealable.

Another feature or aspect of an embodiment is believed at the time of the filing of this patent application to possibly reside broadly in the device, wherein the valve or distributor is at least partially made of at least one of: ruby, sapphire, tantalum, and titanium.

Yet another feature or aspect of an embodiment is believed at the time of the filing of this patent application to possibly reside broadly in the device, wherein said device comprises a deformation of the housing wall for prestressing to a degree that is one of (i) and (ii), wherein (i) and (ii) are: (i) equal to twice the wall thickness of the housing; and (ii) up to 0.1 millimeter.

Still another feature or aspect of an embodiment is believed at the time of the filing of this patent application to possibly reside broadly in the device, wherein said device comprises the use of a pressable housing wall or a pressable cover with a thickness of one of (iii) and (iv), wherein (iii) and (iv) are: (iii) up to 0.5 millimeter; and (iv) up to 0.2 millimeter.

A further feature or aspect of an embodiment is believed at the time of the filing of this patent application to possibly reside broadly in the device, wherein the housing or the deformable wall of the housing comprises a metal comprising titanium or a titanium alloy.

Another feature or aspect of an embodiment is believed at the time of the filing of this patent application to possibly reside broadly in the device, wherein said device comprises the use of magnets with: a diameter of one of (v) and (vi), wherein (v) and (vi) are: (v) up to three millimeters; and (vi)

up to one millimeter; and a height of one of (vi) and (vii), wherein (vi) and (vii) are: (vi) up to five millimeters; and (vii) up to two millimeters.

Yet another feature or aspect of an embodiment is believed at the time of the filing of this patent application to possibly reside broadly in the device, wherein at least one of (viii) and (ix), wherein (viii) and (ix) are: (viii) the magnets in the externally lying adjustment device are at a distance from one another that deviates from the magnets in the internally lying adjustment device by one of one of (x) and (xi), wherein (x) and (xi) are: (x) at most three millimeters; and (xi) at most one millimeter; and (ix) the magnets are distanced apart by one of (xii), (xiii), and (xiv), wherein (xii), (xiii), and (xiv) are: (xii) at most twenty millimeters; (xiii) at most ten millimeters; and (xiv) at most eight millimeters.

Still another feature or aspect of an embodiment is believed at the time of the filing of this patent application to possibly reside broadly in the device, wherein the internally lying adjustment device possesses a spring in the form of a metallic wire or sheet, whose cross section is circular or rectangular and whose diameter or thickness is one of (xv), (xvi), and (xvii), wherein (xv), (xvi), and (xvii) are: (xv) up to 0.5 millimeters; (xvi) up to 0.3 millimeters; and (xvii) up to 0.2 millimeters.

A further feature or aspect of an embodiment is believed at the time of the filing of this patent application to possibly reside broadly in the device, wherein the spring bar is designed as one of (A) and (B), wherein (A) and (B) are: (A) a single-armed lever; and (B) a two-armed lever, of which one lever arm presses against the adjustment plate and whose other lever arm presses against the valve ball or valve cap of the valve or distributor in operative connection.

Another feature or aspect of an embodiment is believed at the time of the filing of this patent application to possibly reside broadly in the device, wherein the valve or distributor has: an external diameter of one of (xviii) and (xix), wherein (xviii) and (xix) are: (xviii) up to thirty-one millimeters; and (xix) up to twenty millimeters; and a height of one of (xx) and (xxi), wherein (xx) and (xxi) are: (xx) up to ten millimeters; and (xxi) up to six millimeters.

The components disclosed in the various publications, disclosed or incorporated by reference herein, may possibly be used in possible embodiments of the present invention, as well as equivalents thereof.

The purpose of the statements about the technical field is generally to enable the Patent and Trademark Office and the public to determine quickly, from a cursory inspection, the nature of this patent application. The description of the technical field is believed, at the time of the filing of this patent application, to adequately describe the technical field of this patent application. However, the description of the technical field may not be completely applicable to the claims as originally filed in this patent application, as amended during prosecution of this patent application, and as ultimately allowed in any patent issuing from this patent application. Therefore, any statements made relating to the technical field are not intended to limit the claims in any manner and should not be interpreted as limiting the claims in any manner.

The appended drawings in their entirety, including all dimensions, proportions and/or shapes in at least one embodiment of the invention, are accurate and are hereby included by reference into this specification.

The background information is believed, at the time of the filing of this patent application, to adequately provide background information for this patent application. However, the background information may not be completely applicable to the claims as originally filed in this patent application, as amended during prosecution of this patent application, and as ultimately allowed in any patent issuing from this patent application. Therefore, any statements made relating to the background information are not intended to limit the claims in any manner and should not be interpreted as limiting the claims in any manner.

All, or substantially all, of the components and methods of the various embodiments may be used with at least one embodiment or all of the embodiments, if more than one embodiment is described herein.

The purpose of the statements about the object or objects is generally to enable the Patent and Trademark Office and the public to determine quickly, from a cursory inspection, the nature of this patent application. The description of the object or objects is believed, at the time of the filing of this patent application, to adequately describe the object or objects of this patent application. However, the description of the object or objects may not be completely applicable to the claims as originally filed in this patent application, as amended during prosecution of this patent application, and as ultimately allowed in any patent issuing from this patent application. Therefore, any statements made relating to the object or objects are not intended to limit the claims in any manner and should not be interpreted as limiting the claims in any manner.

All of the patents, patent applications and publications recited herein, and in the Declaration attached hereto, are hereby incorporated by reference as if set forth in their entirety herein.

The summary is believed, at the time of the filing of this patent application, to adequately summarize this patent application. However, portions or all of the information contained in the summary may not be completely applicable to the claims as originally filed in this patent application, as amended during prosecution of this patent application, and as ultimately allowed in any patent issuing from this patent application. Therefore, any statements made relating to the summary are not intended to limit the claims in any manner and should not be interpreted as limiting the claims in any manner.

It will be understood that the examples of patents, published patent applications, and other documents which are included in this application and which are referred to in paragraphs which state "Some examples of . . . which may possibly be used in at least one possible embodiment of the present application . . . " may possibly not be used or useable in any one or more embodiments of the application.

The sentence immediately above relates to patents, published patent applications and other documents either incorporated by reference or not incorporated by reference.

All of the patents, patent applications or patent publications, which were cited in the International Search Report dated Oct. 13, 2009, and/or cited elsewhere are hereby incorporated by reference as if set forth in their entirety herein as follows: US 2005/245858, having the title "Branching catheter systems with diagnostic components," and published on Nov. 3, 2005; US 2007/078398, having the title "Multibranched anti-reflux valve," and published on Apr. 5, 2007; U.S. Pat. No. 6,689,085, having the title "Method and apparatus for treating adult-onset dementia of the Alzheimer's type," published on Feb. 10, 2004; and US 2005/245887, having the title "Catheter systems having flow restrictors," published on Nov. 3, 2005.

The patents, patent applications, and patent publication listed above in the preceding paragraphs are herein incorporated by reference as if set forth in their entirety. The purpose of incorporating U.S. patents, Foreign patents, publications, etc. is solely to provide additional information relating to technical features of one or more embodiments, which information may not be completely disclosed in the wording in the pages of this application. Words relating to the opinions and judgments of the author and not directly relating to the technical details of the description of the embodiments therein are not incorporated by reference. The words all, always, absolutely, consistently, preferably, guarantee, particularly, constantly, ensure, necessarily, immediately, endlessly, avoid, exactly, continually, expediently, ideal, need, must, only, perpetual, precise, perfect, require, requisite, simultaneous, total, unavoidable, and unnecessary, or words substantially equivalent to the above-mentioned words in this sentence, when not used to describe technical features of one or more embodiments, are not considered to be incorporated by reference herein.

The corresponding foreign and international patent publication applications, namely, Federal Republic of Germany Patent Application No. 10 2008 030 942.7, filed on Jul. 2, 2008, having inventors Christoph MIETHKE and Ullrich MEIER, and DE-OS 10 2008 030 942.7 and DE-PS 10 2008 030 94 2.7, and International Application No. PCT/EP2008/004751, filed on Jul. 1, 2009, having WIPO Publication No. WO2010/000461 and inventors Christoph MIETHKE and Ullrich MEIER, are hereby incorporated by reference as if set forth in their entirety herein for the purpose of correcting and explaining any possible misinterpretations of the English translation thereof. In addition, the published equivalents of the above corresponding foreign and international patent publication applications, and other equivalents or corresponding applications, if any, in corresponding cases in the Federal Republic of Germany and elsewhere, and the references and documents cited in any of the documents cited herein, such as the patents, patent applications and publications, are hereby incorporated by reference as if set forth in their entirety herein.

The purpose of incorporating the corresponding foreign equivalent patent application(s), that is, PCT/EP2008/004751 and German Patent Application 10 2008 030 942.7, is solely for the purpose of providing a basis of correction of any wording in the pages of the present application, which may have been mistranslated or misinterpreted by the translator. Words relating to opinions and judgments of the author and not directly relating to the technical details of the description of the embodiments therein are not to be incorporated by reference. The words all, always, absolutely, consistently, preferably, guarantee, particularly, constantly, ensure, necessarily, immediately, endlessly, avoid, exactly, continually, expediently, ideal, need, must, only, perpetual, precise, perfect, require, requisite, simultaneous, total, unavoidable, and unnecessary, or words substantially equivalent to the above-mentioned word in this sentence, when not used to describe technical features of one or more embodiments, are not generally considered to be incorporated by reference herein.

Statements made in the original foreign patent applications PCT/EP2008/004751 and DE 10 2008 030 942.7 from which this patent application claims priority which do not have to do with the correction of the translation in this patent application are not to be included in this patent application in the incorporation by reference.

Any statements about admissions of prior art in the original foreign patent applications PCT/EP2008/004751 and DE 10 2008 030 942.7 are not to be included in this patent application in the incorporation by reference, since the laws relating to prior art in non-U.S. Patent Offices and courts may be substantially different from the Patent Laws of the United States.

All of the references and documents, cited in any of the documents cited herein, are hereby incorporated by reference as if set forth in their entirety herein. All of the documents cited herein, referred to in the immediately preceding sentence, include all of the patents, patent applications and publications cited anywhere in the present application.

The description of the embodiment or embodiments is believed, at the time of the filing of this patent application, to adequately describe the embodiment or embodiments of this patent application. However, portions of the description of the embodiment or embodiments may not be completely applicable to the claims as originally filed in this patent application, as amended during prosecution of this patent application, and as ultimately allowed in any patent issuing from this patent application. Therefore, any statements made relating to the embodiment or embodiments are not intended to limit the claims in any manner and should not be interpreted as limiting the claims in any manner.

The details in the patents, patent applications and publications may be considered to be incorporable, at applicant's option, into the claims during prosecution as further limitations in the claims to patentably distinguish any amended claims from any applied prior art.

The purpose of the title of this patent application is generally to enable the Patent and Trademark Office and the public to determine quickly, from a cursory inspection, the nature of this patent application. The title is believed, at the time of the filing of this patent application, to adequately reflect the general nature of this patent application. However, the title may not be completely applicable to the technical field, the object or objects, the summary, the description of the embodiment or embodiments, and the claims as originally filed in this patent application, as amended during prosecution of this patent application, and as ultimately allowed in any patent issuing from this patent application. Therefore, the title is not intended to limit the claims in any manner and should not be interpreted as limiting the claims in any manner.

The abstract of the disclosure is submitted herewith as required by 37 C.F.R. §1.72(b). As stated in 37 C.F.R. §1.72 (b):

> A brief abstract of the technical disclosure in the specification must commence on a separate sheet, preferably following the claims, under the heading "Abstract of the Disclosure." The purpose of the abstract is to enable the Patent and Trademark Office and the public generally to determine quickly from a cursory inspection the nature and gist of the technical disclosure. The abstract shall not be used for interpreting the scope of the claims.

Therefore, any statements made relating to the abstract are not intended to limit the claims in any manner and should not be interpreted as limiting the claims in any manner.

The embodiments of the invention described herein above in the context of the preferred embodiments are not to be taken as limiting the embodiments of the invention to all of the provided details thereof, since modifications and variations thereof may be made without departing from the spirit and scope of the embodiments of the invention.

What is claimed is:

1. A method of draining cerebrospinal fluid comprising:
   installing, in a patient having excess cerebrospinal fluid in his or her cranial cavity, a cerebrospinal fluid drainage device comprising at least three tubes and a distributor that connects said at least three tubes, wherein said at least three tubes comprise a supply tube, a first discharge tube, and a second discharge tube;
   draining cerebrospinal fluid from the head of a patient through said supply tube toward said distributor;

shifting a rotary device of said distributor to a first position, and thereby flowing cerebrospinal fluid from said supply tube, through said distributor, and to said first discharge tube, and blocking flow of cerebrospinal fluid to said second discharge tube; and upon formation of a blockage of flow in said first discharge tube, shifting said rotary device to a second position, and thereby flowing cerebrospinal fluid from said supply tube, through said distributor, and to said second discharge tube, and blocking flow of cerebrospinal fluid to said first discharge tube.

2. The method according to claim 1, wherein said method further comprises shifting said rotary device to a third position, and thereby blocking flow of cerebrospinal fluid to both said first discharge tube and said second discharge tube.

3. The method according to claim 2, wherein each of said steps of blocking flow of cerebrospinal fluid comprises placing a portion of said rotary device at an opening in a housing of said distributor that houses said rotary device, to which opening is connected one of said discharge tubes, and thereby totally or partially sealing said opening in said housing to minimize or prevent flow of cerebrospinal fluid therethrough.

4. A cerebrospinal fluid drainage device for performing the method according to claim 1, comprising:
   at least three tubes comprising a supply tube configured to receive cerebrospinal fluid, a first discharge tube configured to discharge cerebrospinal fluid, and a second discharge tube configured to discharge cerebrospinal fluid;
   a distributor configured to control flow of cerebrospinal fluid;
   said at least three tubes being connected by said distributor;
   said distributor comprises a rotary device which is shiftable between:
      a first position in which said rotary device permits flow of cerebrospinal fluid from said supply tube to said first discharge tube, and blocks flow to said second discharge tube; and
      a second position in which said rotary device permits flow of cerebrospinal fluid from said supply tube to said second discharge tube, and blocks flow to said first discharge tube; and
   said rotary device comprising magnets or magnetic portions configured to be engaged by an adjusting device to permit shifting of said rotary device by magnetic force.

5. The device according to claim 4, wherein said distributor comprises a substantially flat housing to permit installation completely under the skin of a patient.

6. The device according to claim 5, wherein said device further comprises an external adjusting unit configured to provide a magnetic adjusting force through the skin of a patient to shift said rotary device.

7. The device according to claim 4, wherein said device further comprises an external adjusting unit configured to provide a magnetic adjusting force through the skin of a patient to shift said rotary device.

8. The device according to claim 4, wherein said rotary device is additionally shiftable to a third position in which said rotary device blocks flow of cerebrospinal fluid to both said first discharge tube and said second discharge tube.

9. The device according to claim 8, wherein:
   said distributor comprises a housing which houses said rotary device;
   said housing comprises openings which connect said tubes to the interior of said housing; and
   said rotary device is configured to totally or partially seal one or more of said openings in said housing to control flow of cerebrospinal fluid to said discharge tubes.

10. The cerebrospinal fluid drainage device for performing the method according to claim 1, comprising:
    at least three tubes comprising a supply tube configured to receive cerebrospinal fluid, a first discharge tube configured to discharge cerebrospinal fluid, and a second discharge tube configured to discharge cerebrospinal fluid;
    a distributor configured to control flow of cerebrospinal fluid;
    said at least three tubes being connected by said distributor;
    said distributor comprises a rotary device which is shiftable between:
       a first position in which said rotary device permits flow of cerebrospinal fluid from said supply tube to said first discharge tube, and blocks flow to said second discharge tube; and
       a second position in which said rotary device permits flow of cerebrospinal fluid from said supply tube to said second discharge tube, and blocks flow to said first discharge tube; and
    an external adjusting unit configured to provide a magnetic adjusting force through the skin of a patient to shift said rotary device.

11. The device according to claim 10, wherein said device further comprises an external adjusting unit configured to provide a magnetic adjusting force through the skin of a patient to shift said movable distributor.

12. A method of draining cerebrospinal fluid comprising:
    installing, in a patient having excess cerebrospinal fluid in his or her cranial cavity, a cerebrospinal fluid drainage device comprising at least three tubes and a valve that connects said at least three tubes, wherein said at least three tubes comprise a first supply tube, a second supply tube, and a discharge tube;
    draining cerebrospinal fluid from the head of a patient through said supply tubes toward said valve;
    shifting a movable distributor of said valve to a first position, and thereby flowing cerebrospinal fluid from said first supply tube, through said valve, and to said discharge tube, and blocking flow of cerebrospinal fluid from said second supply tube; and
    upon formation of a blockage of flow in said first supply tube, shifting said movable distributor to a second position, and thereby flowing cerebrospinal fluid from said second supply tube, through said valve, and to said discharge tube, and blocking flow of cerebrospinal fluid from said first supply tube.

13. The method according to claim 12, wherein said method further comprises shifting said movable distributor to a third position, and thereby blocking flow of cerebrospinal fluid from both said first supply tube and said second supply tube.

14. The method according to claim 13, wherein each of said steps of blocking flow of cerebrospinal fluid comprises placing a portion of said movable distributor at an opening in a housing of said valve that houses said movable distributor, to which opening is connected one of said supply tubes, and thereby totally or partially sealing said opening in said housing to minimize or prevent flow of cerebrospinal fluid therethrough.

15. A device for draining cerebrospinal fluid comprising:
    at least three tubes comprising a first supply tube configured to receive cerebrospinal fluid, a second supply tube configured to receive cerebrospinal fluid, and a discharge tube configured to discharge cerebrospinal fluid;
    a valve configured to control flow of cerebrospinal fluid;
    said at least three tubes being connected by said valve;

said valve comprises a movable distributor which is shiftable between:
  a first position in which said movable distributor permits flow of cerebrospinal fluid from said first supply tube to said discharge tube, and blocks flow from said second supply tube; and
  a second position in which said movable distributor permits flow of cerebrospinal fluid from said second supply tube to said discharge tube, and blocks flow from said first supply tube; and
said movable distributor comprising magnets or magnetic portions configured to be engaged by an adjusting device to permit shifting of said movable distributor by magnetic force.

16. The device according to claim 15, wherein said movable distributor is additionally shiftable to a third position in which said movable distributor blocks flow of cerebrospinal fluid from both said first supply tube and said second supply tube.

17. The device according to claim 15, wherein said valve distributor comprises a substantially flat housing to permit installation completely under the skin of a patient.

18. The device according to claim 15, wherein said device further comprises an external adjusting unit configured to provide a magnetic adjusting force through the skin of a patient to shift said movable distributor.

* * * * *